US012226249B2

(12) United States Patent
van Kampen

(10) Patent No.: US 12,226,249 B2
(45) Date of Patent: Feb. 18, 2025

(54) SYSTEMS AND METHODS FOR ANNOTATING X-RAYS

(71) Applicant: XORAN TECHNOLOGIES, LLC, Ann Arbor, MI (US)

(72) Inventor: William van Kampen, Saline, MI (US)

(73) Assignee: Xoran Technologies, LLC, Ann Arbor, MI (US)

( * ) Notice: Subject to any disclaimer, the term of this patent is extended or adjusted under 35 U.S.C. 154(b) by 218 days.

(21) Appl. No.: 18/097,929

(22) Filed: Jan. 17, 2023

(65) Prior Publication Data

US 2023/0225689 A1 Jul. 20, 2023

Related U.S. Application Data

(60) Provisional application No. 63/299,650, filed on Jan. 14, 2022.

(51) Int. Cl.
*A61B 6/02* (2006.01)
*A61B 6/00* (2006.01)
(Continued)

(52) U.S. Cl.
CPC ............... *A61B 6/482* (2013.01); *A61B 6/02* (2013.01); *A61B 6/032* (2013.01); *A61B 6/468* (2013.01);
(Continued)

(58) Field of Classification Search
CPC .. A61B 6/02; A61B 6/032; A61B 6/12; A61B 6/4085; A61B 6/4405; A61B 6/468;
(Continued)

(56) References Cited

U.S. PATENT DOCUMENTS 10,886,029 B2 * 1/2021 Abedin ................... G06F 3/011
2014/0112444 A1 * 4/2014 Imagawa ............. A61B 6/4441
378/62
(Continued)

FOREIGN PATENT DOCUMENTS

CN 117831700 A * 4/2024
EP 4404205 A1 * 7/2024 ............. G06T 15/00

OTHER PUBLICATIONS

English translation of CN-117831700-A (Year: 2024).*

*Primary Examiner* — Mark R Gaworecki
(74) *Attorney, Agent, or Firm* — K&L Gates LLP

(57) ABSTRACT

A system for tracking an instrument during a procedure on a patient is provided. The system includes a rotatable gantry, an x-ray imaging device, a processor, and a memory coupled to the processor. The processor is configured to: generate a three dimensional (3D) image based on a plurality of initial x-ray projections taken at a plurality of projection angles; generate an annotated 3D image of the 3D image including annotations of the target location and at least one planned instrument path on the 3D image; generate a plurality of two dimensional (2D) annotations based on the annotated 3D image at each projection angle; superimpose each 2D annotation onto the initial x-ray projection of the corresponding projection angle; obtain a plurality of subsequent x-ray projections of the patient at the plurality of projection angles; and co-register each subsequent x-ray projection with a corresponding annotated initial x-ray projection for each projection angle.

10 Claims, 9 Drawing Sheets

(51) Int. Cl.
*A61B 6/03* (2006.01)
*A61B 6/46* (2024.01)
*A61B 6/12* (2006.01)
*A61B 6/40* (2024.01)

(52) U.S. Cl.
CPC .............. *A61B 6/487* (2013.01); *A61B 6/488* (2013.01); *A61B 6/5235* (2013.01); *A61B 6/12* (2013.01); *A61B 6/4085* (2013.01); *A61B 6/4405* (2013.01); *G06T 2207/10* (2013.01)

(58) Field of Classification Search
CPC ......... A61B 6/482; A61B 6/487; A61B 6/488; A61B 6/5235; G06T 2207/10
See application file for complete search history.

(56) References Cited

U.S. PATENT DOCUMENTS

2019/0180488 A1* 6/2019 Hoernig .................... G06T 7/70
2023/0021332 A1* 1/2023 Vaillant .................... G06T 7/97

* cited by examiner

SYSTEMS AND METHODS FOR ANNOTATING X-RAYS

CROSS-REFERENCE TO RELATED APPLICATIONS

This application claims the benefit of U.S. Provisional Application No. 63/299,650 filed Jan. 14, 2022, the entirety of which is hereby incorporated by reference.

BACKGROUND OF THE INVENTION

Cone-beam computed tomography (CBCT) systems generate three-dimensional images by tomographically reconstructing the volume from a series of x-ray projections taken at a series of angles as the x-ray imaging device orbits the patient. These x-ray projection images are similar to the x-ray images often acquired for fluoroscopic image guidance during a surgical procedure but with additional detail.

Separately, in fluoroscopic image guidance, a series of x-ray projections are taken as the surgical instrument is moved within the patient. The x-ray projections enable the physician to see how the instrument is moving within the patient's body. For example, a biopsy needle can be seen while it is being moved into the lungs to poke at a nodule and take a sample for analysis. The needle is easily seen on the x-ray projection because it is metal and has a clear shadow. However, the soft tissue nodules can be hard or impossible to see on the x-ray projection of the fluoroscopic image guidance. The inability to view the soft tissue nodule makes the targeting difficult or impossible, especially in complex three-dimensional (3D) orientations.

For example, lung nodule biopsies are challenging to complete successfully. Conventional tracking systems utilize two dimensional (2D) imaging tools such as a bronchoscope, ultrasound, and CT x-ray projections. Fluoroscopy x-ray projections taken during the procedure show the needle but not the nodule target, while the nodule is visible only on ultrasound imaging and not x-ray projections. The physician uses x-ray imaging to move the needle while guesstimating the location of the soft tissue nodule to be biopsied based on the ultrasound imaging. The process is further complicated by the patient's respiratory movement.

Accordingly, there is a need for imaging systems and methods that enable the physician to view the soft tissue nodule and the surgical instrument during the procedure.

BRIEF SUMMARY OF THE INVENTION

The present invention relates to imaging systems and methods that enable the physician to view the soft tissue nodule and the surgical instrument during a procedure. The presently disclosed imaging systems and methods provide for the generation of annotated images including identification of a target nodule and a planned instrument path for use during the procedure to increase the likelihood of a successful sample collection. Conventional fluoroscopy x-ray imaging that is typically used by the physician to view the location of the instrument during use does not include soft tissue nodules or areas to be biopsied because those elements are virtually undetectable or not reliably detectable on x-ray projections. The present system uses more detailed imaging to create annotations of the target area and adds the annotations to the fluoroscopy x-ray image so that the physician can view the instrument relative to the target location and the planned instrument path during the procedure.

The present imaging system includes a rotatable gantry configured to rotate about an axis of rotation and an x-ray imaging device mounted thereto. The system also includes a processor in communication with the x-ray imaging device and a memory coupled to the processor. Generally, the system captures a set of x-ray projections used to generate a three-dimensional (3D) image, which shows the location of the target nodule to be biopsied. The 3D image is then annotated to identify the target nodule or location as well as an access path and/or a planned instrument path for the procedure. The annotations from the annotated 3D image are superimposed onto the original x-ray projections, which are later used as a guide for the physical during the procedure.

During the procedure, the physician tracks movement of the instrument by capturing x-ray images using the x-ray imaging device. To track this movement, the physician positions the x-ray imaging device at an appropriate location along the gantry to provide a view of the planned instrument path toward the target nodule. The physician takes x-ray projections throughout the procedure in order to monitor the location of the instrument.

To help guide the physician, the system combines the annotations from the annotated original x-rays and the subsequent x-ray projections captured during the procedure to generate x-ray projections that show both the instrument and the target location and planned instrument path, among other things. The system co-registers the relevant annotated original x-ray projection with the subsequent x-ray projection collected during the procedure by aligning features common to both x-ray projections. The annotated subsequent x-ray projection enables the physician to guide the instrument through the procedure knowing where the target location is, while such location is not available on the fluoroscopy x-ray projection taken during the procedure.

In one embodiment, the system is configured to capture a plurality of initial x-ray projections taken at a plurality of projection angles in order to generate a three dimensional (3D) image of an area including a target location. The 3D image is then annotated, generating an annotated 3D image of the 3D image. The annotations indicate the target location and at least one planned instrument path on the 3D image. The annotations can be added manually by the user through a user interface or automatically as performed by machine learning-based deep learning network algorithms.

From the annotated 3D image, a plurality of two dimensional (2D) annotations is generated. Each 2D annotation corresponds to a projection angle of the plurality of projection angles. Each 2D annotation is then superimposed onto the initial x-ray projection of the corresponding projection angle to generate a plurality of annotated initial x-ray projections. The plurality of annotated initial x-ray projections may be stored for later use.

Then, after positioning the instrument in the patient, the system 100 obtains a plurality of subsequent x-ray projections of the patient at the plurality of projection angles. The subsequent x-ray projections show the location of the instrument in the patient's body. Each subsequent x-ray projection is the co-registered with the corresponding annotated initial x-ray projection for each projection angle to generate a plurality of annotated subsequent x-ray projections.

One advantage of the present system is the scanning system does not require the use of a larger, CT scanner when acquiring the series of 2D images. The use of the smaller device can accommodate various heights and positioning of patients easily.

Another advantage of the present system is that the system is provided in a relatively small, portable device that can be used common medical procedure rooms where such biopsies take place and do not require expensive and more rarely available technology, such as interventional radiology suites.

A further advantage is that the generation of the tomographic reconstruction can be accomplished on a computer or other basic system and does not require x-ray imaging capabilities on the same device. In other embodiments, all processing is provided on a multi-modality imaging system, including both x-ray and CT scanning. In still further embodiments, the processing occurs on a separate workstation in communication with the imaging system.

BRIEF DESCRIPTION OF THE DRAWINGS

The drawing figures depict one or more implementations in accord with the present concepts, by way of example only, not by way of limitations.

DETAILED DESCRIPTION OF THE INVENTION

Figure 1:
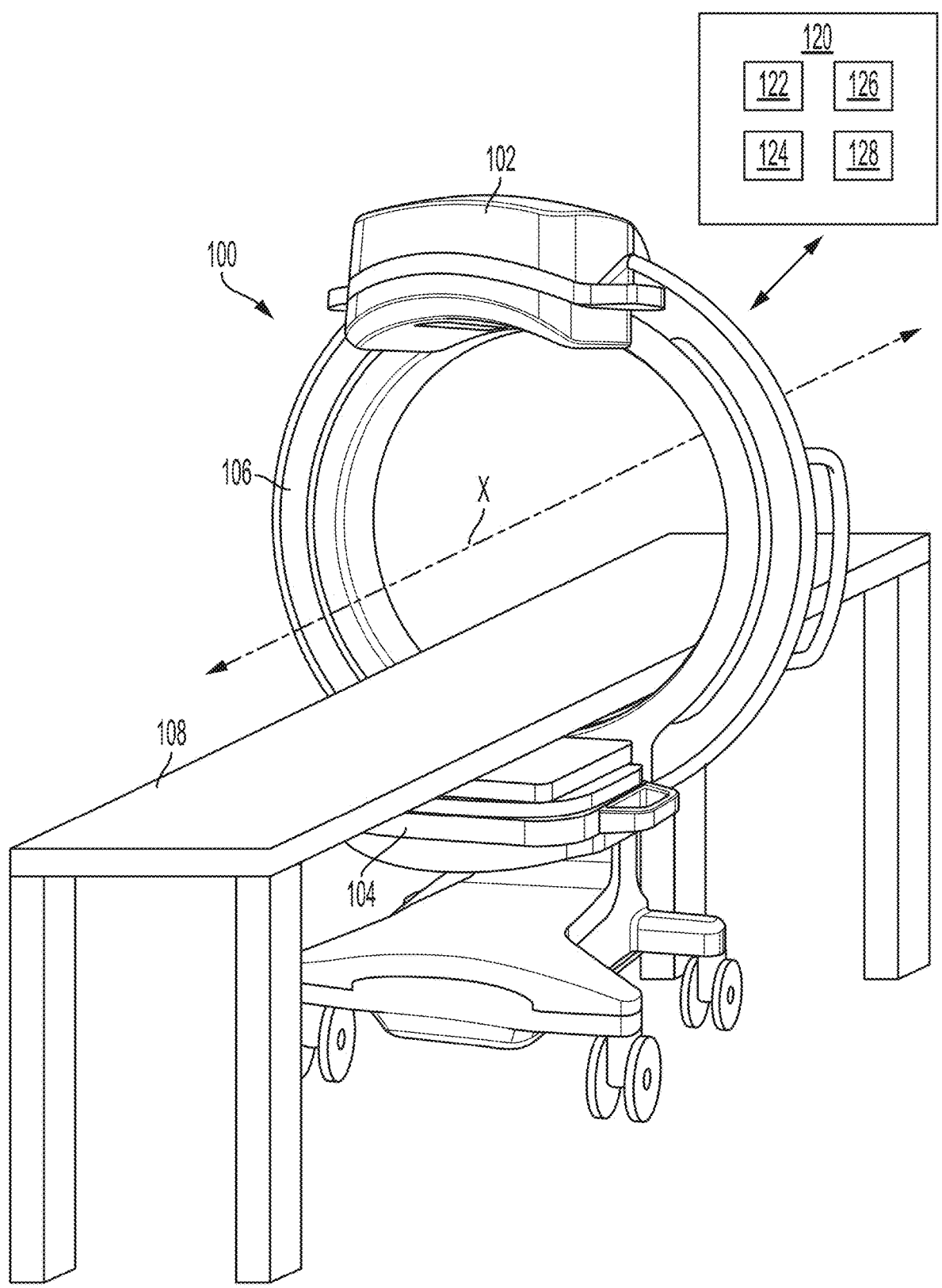
FIG. 1 is a schematic of an imaging system of the present invention.

FIG. 1 illustrates an exemplary imaging system 100 of the present application. As shown in FIG. 1, the imaging system 100 includes an x-ray imaging device 101 including an x-ray source 102 and an x-ray detector 104 mounted onto a ring-shaped gantry 106, which moves along the length of an operating table 108 on which the patient rests during a scanning procedure. The x-ray source 102 and detector 104 are positioned opposite to one another on the gantry 106 and extend outwardly parallel to the floor. A motor rotates the gantry 106 about an axis of rotation X to obtain a plurality of x-ray images of the patient resting on the operating table 108 at a plurality of projection angles. The gantry 106 can be rotated approximately slightly more than 360 degrees about the axis of rotation X.

The imaging system 100 also includes a computer 120 having a display 122, a processor 124, memory 126, and a database or other storage 128. The computer 120 is programmed to perform the functions and to control the functionality and operation of the imaging system 100 in the manner described herein. Generally, through programming of the processor 124, the computer 120 controls the operation of the x-ray imaging device 101 and the annotation of the x-ray projections captured by the x-ray source 102 and deflector 104 as detailed herein.

Figure 2:
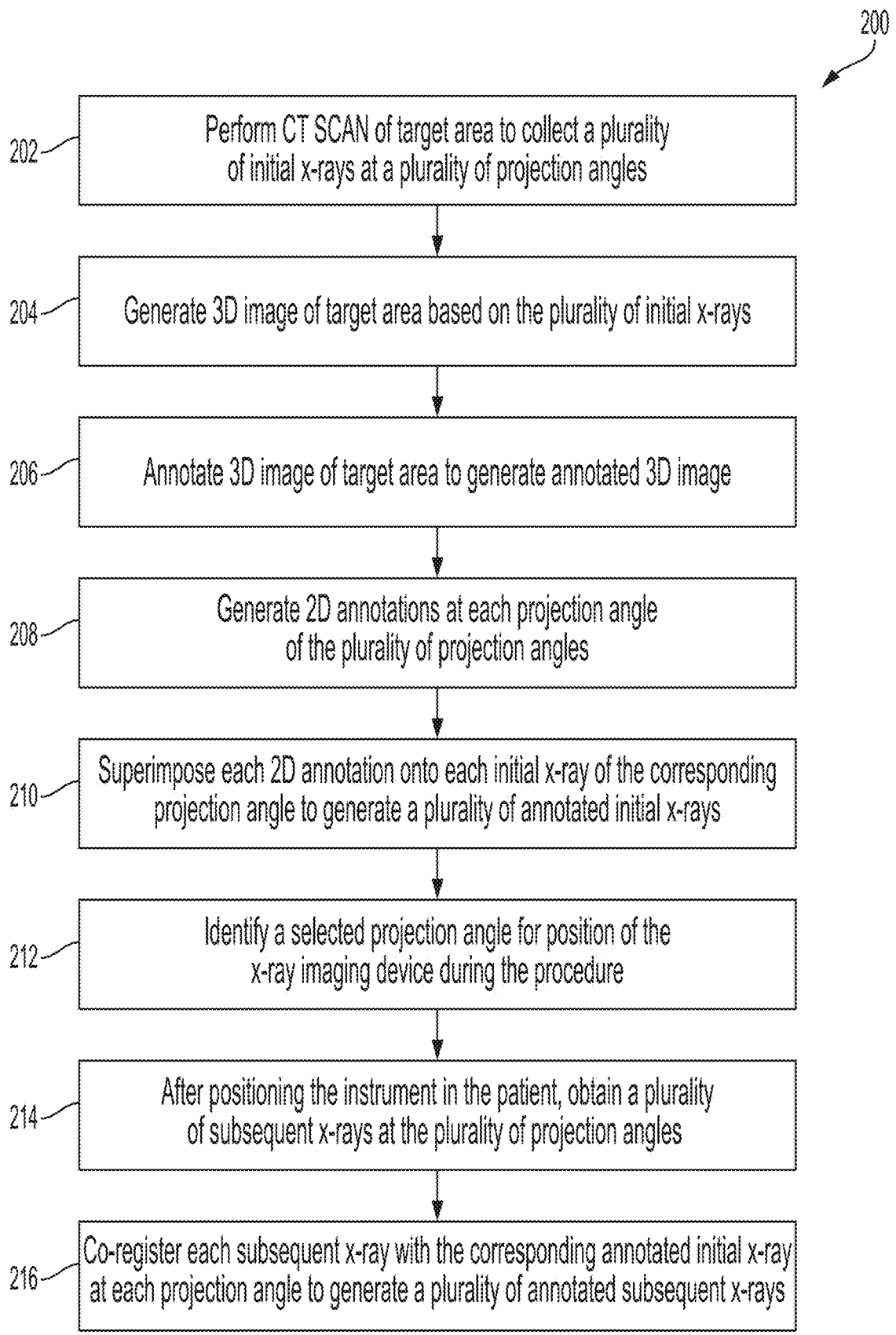
FIG. 2 illustrates an example method of use of the imaging systems of FIG. 1.

Referring to FIG. 2, a method 200 for annotating x-ray projections using the imaging system 100 is illustrated. The following method 200 is illustrated in terms of a lung nodule biopsy, although it should be understood that the method may be utilized in other situations and procedures involving any target location. Additionally, the drawings illustrate access to a soft tissue module for a lung nodule biopsy being access through the patient's main windpipe. It should be understood that instrument paths utilizing the subject matter disclosed herein require access to very small distal bronchioles which require a more complex access path than the illustrated access path.

Figure 3A:
FIGS. 3A and 3B are an example 3D image and an example of one of the initial x-ray projections used to generate the 3D image, both generated by the imaging system of FIG. 1.

The method 200 begins at step 202, where an appropriate CT scan of the patient is obtained using the imaging system 100. During the CT scan, the x-ray imaging device 101 captures x-ray images of the patient as it rotates around the axis of rotation X. In step 204, a 3D volumetric image 150 as shown in FIG. 3A is generated using a plurality of initial x-ray projections 152 captured by the x-ray imaging device 101 of the imaging system 100 during the CT scan. As in a conventional CT scan, the computer 120 generates the plurality of initial x-ray projections 152 taken by the x-ray detector 104 and sends the initial x-ray projections 152 to the computer 120 to generate a 3D volumetric image 154 of an area to be accessed during the procedure.

Figure 3B:
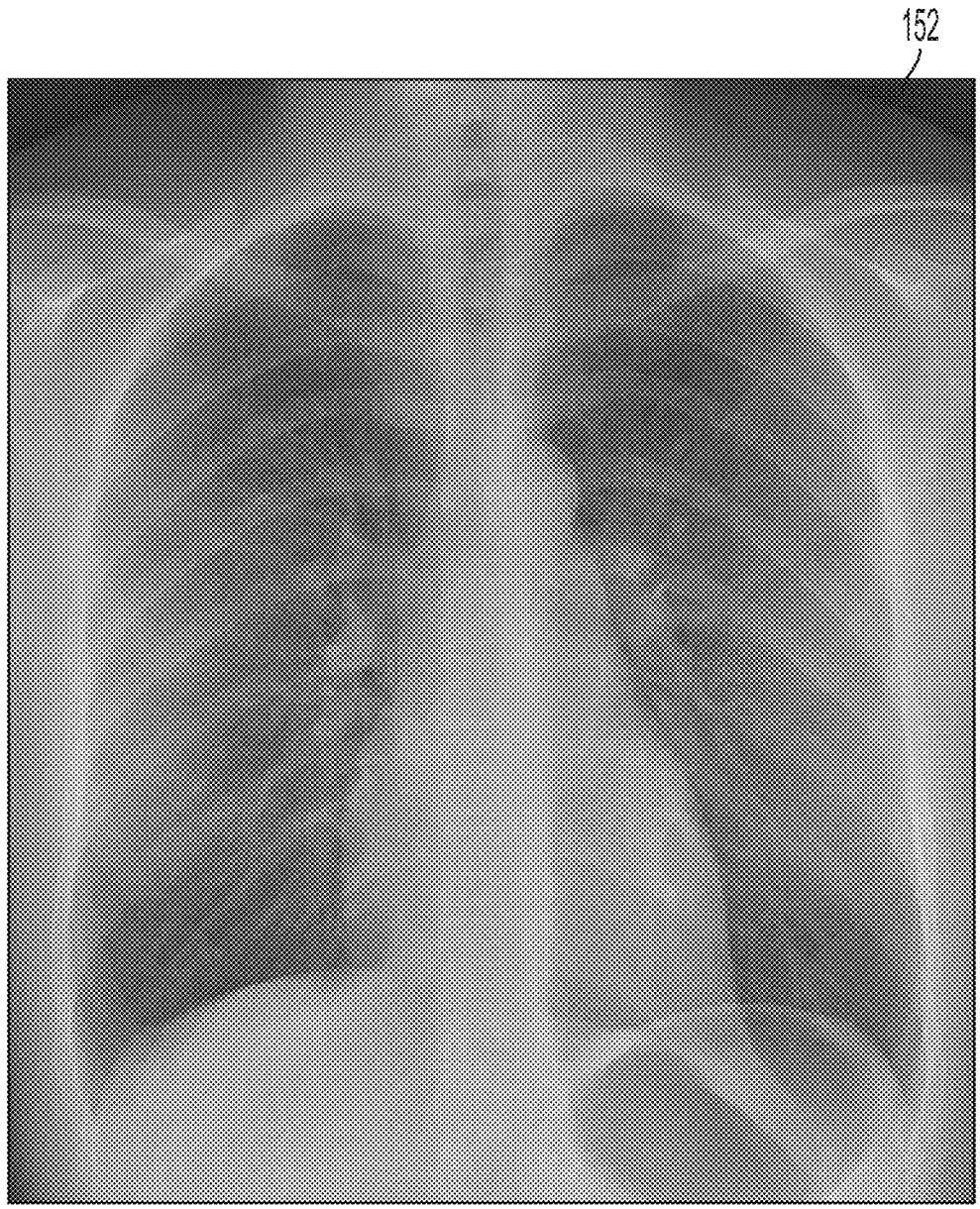

As shown in the example 3D volumetric image 150 and the example initial x-ray projection 152 of FIGS. 3A and 3B, the 3D volumetric image 150 and initial x-ray projections 152 typically provide imaging of numerous areas of the human body, including but not limited to bones and organs. In many cases, the 3D volumetric image 150 also shows relatively indiscernible elements, such as soft tissue, that are not shown clearly on a conventional 2D fluoroscopy x-ray projection.

Figure 4:
FIG. 4 is an example annotated 3D image generated by the imaging system of FIG. 1.

In the next step 206, the user annotates the 3D volumetric image 152 to identify and/or label a target location such as a soft tissue nodule and an access path to the target location. FIG. 4 illustrates the annotated 3D image 154 including identification of the lungs, the heart, the target location, an access path to the target location, and a planned instrument path. The identification appears on the annotated 3D image 154 as indicated by the annotations 156.

In some embodiments, the system 100 includes a user interface configured to receive user input from the operator or physician to identify and/or label the elements to be annotated. In other embodiments, the system 100 automatically identifies the elements and adds boundary lines, call-outs, labels, and/or any other identifying information based on machine learning or other modeling. Still further embodiments of the system 100 allow for combinations of manual and automatic annotating. In some embodiments, the system automatically provides an initial guess or recommendation, sometimes including a confidence metric, and allows the user to make adjustments as needed.

Figure 5:
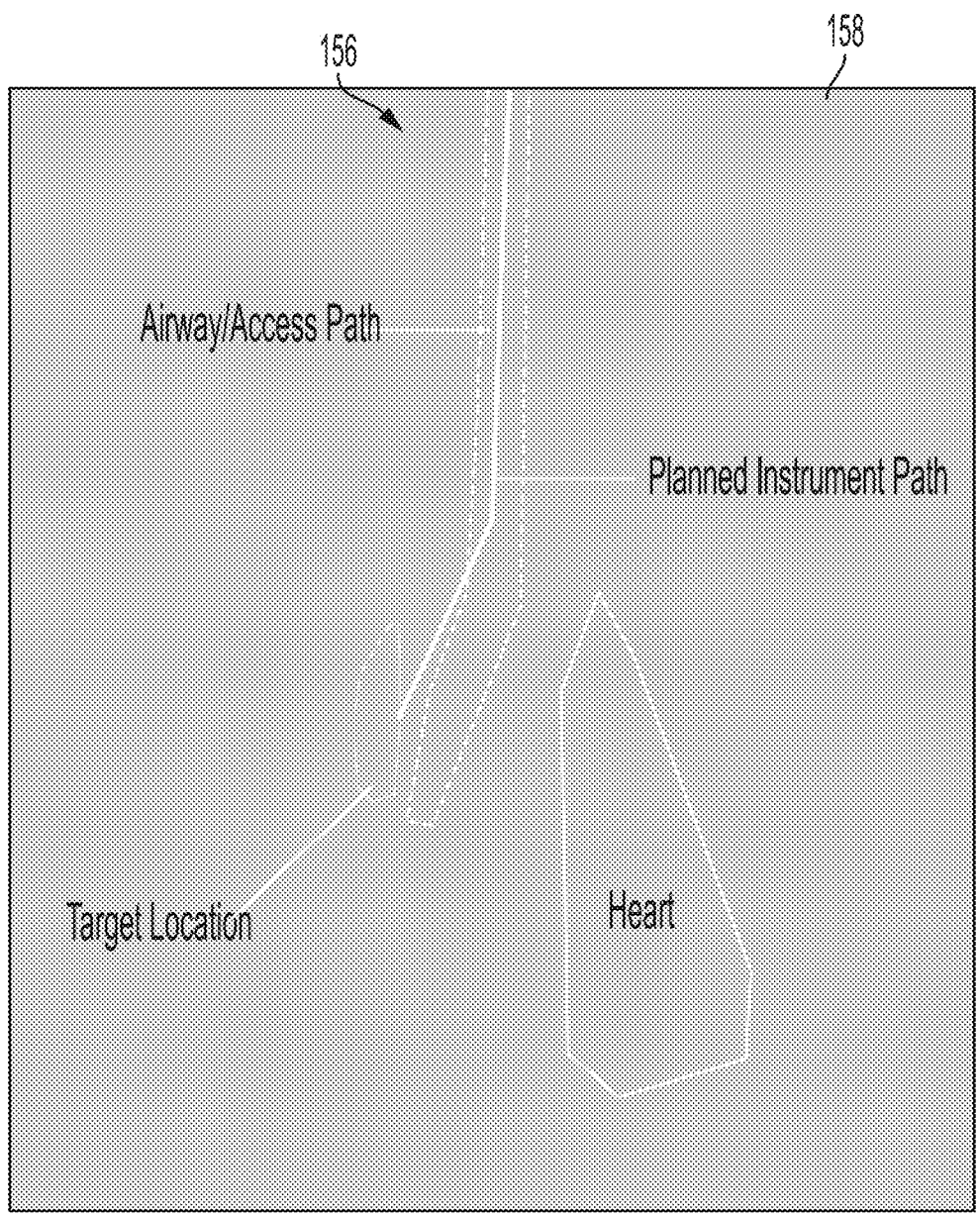
FIG. 5 is an example 2D annotation generated by the imaging system of FIG. 1.

The annotations 156 that appear in the annotated 3D volumetric image 156 shown in FIG. 4 may also be shown in each two-dimensional view of each initial x-ray projection 152 as well. In step 208, the annotations 156 of the 3D volumetric image 154 from step 204 are projected into a two-dimensional format for each projection angle of the plurality of initial x-ray projections 152 used to generate the 3D volumetric image 150. FIG. 5 illustrates an exemplary 2D annotation 158 showing the annotations 156 taken at one of the projection angles. In some embodiments, the plurality of 2D annotations 158 is stored in the database for subsequent use.

Figure 6:
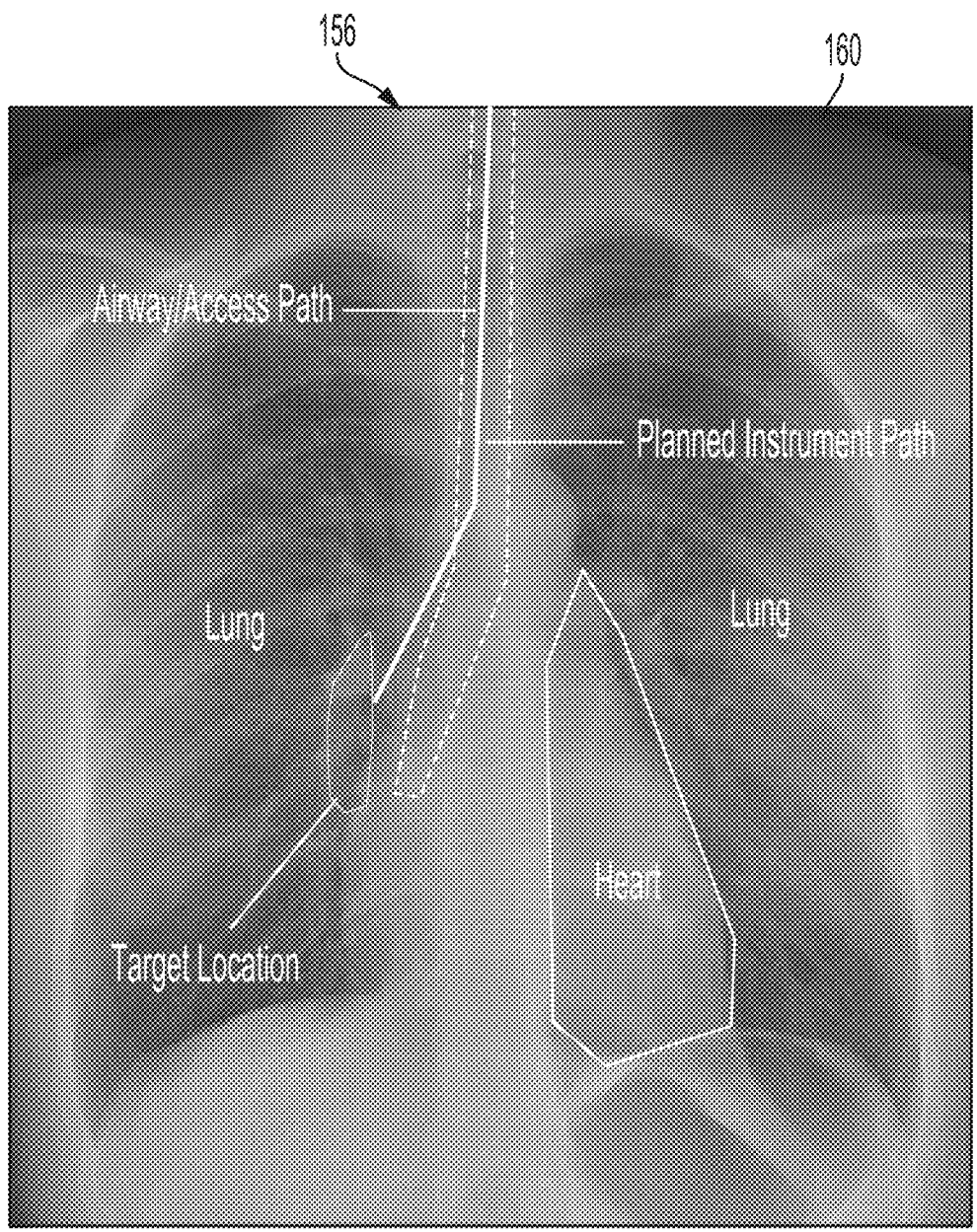
FIG. 6 is an example annotated x-ray projection generated by the imaging system of FIG. 1.

In step 210, the system 100 superimposes each 2D annotation 158 onto the initial x-ray projection 152 of the corresponding projection angle for each of the plurality of projection angles to generate a plurality of annotated initial x-ray projections 160. As seen in FIG. 6, the annotated initial x-ray projection 160 may include annotations 156 indicating the lungs and the heart as well as the target location, an access path to the target location, and potentially at least one planned instrument path. The annotated initial x-ray projections 160 may be stored in the database. Superimposing the 2D annotations 158 onto the initial x-ray projection 152 may be done manually by a user or operator or automatically by the computer 120.

In some embodiments, the annotations 156 include a plurality of planned instrument paths, each planned instrument path being an option path to be evaluated by the physician and/or system 100. Prior to the procedure, the physician and/or system 100 may evaluate the plurality of planned instrument paths to determine which path allows for the instrument to access the target location with the greatest likelihood for a successful sample collection. For example, the physician may review the plurality of annotated initial x-ray projections 160 to compare the angle of the instrument poking the nodule for sample collection, the ability of the instrument to easily move through the access path and/or other areas to reach the target area, the spacing of the instrument from high value organs such as the heart, the optimal angle to allow visualization of the poke path or planned instrument path relative to the target location, and other factors. In other embodiments, the system 100 automatically evaluates the plurality of planned instrument paths based on a plurality of path factors programmed into the computer 120 and identifies a preferred instrument path and/or provides an initial evaluation for physician review.

Referring to steps 204-210, the 3D volumetric image 150 provides more detail in the scan than is provided by the x-ray projections because the 3D volumetric image compiles and integrates details from a large number of x-ray projections, enabling the visualization of more subtle structures such as soft tissue as well as their location in a three-dimensional space instead of simply 2D. The 2D x-ray projections lack this contrast detail that is provided in the 3D volumetric image. The 2D projections also cannot show the occluding anatomy in front of and behind the point of interest shown along the plane at which the x-ray image was captured. It is far more reliable to annotate the target location and other aspects in the 3D image 150 and project the annotations onto the 2D x-ray projection instead of annotating the 2D x-ray projection direction.

Figure 7:
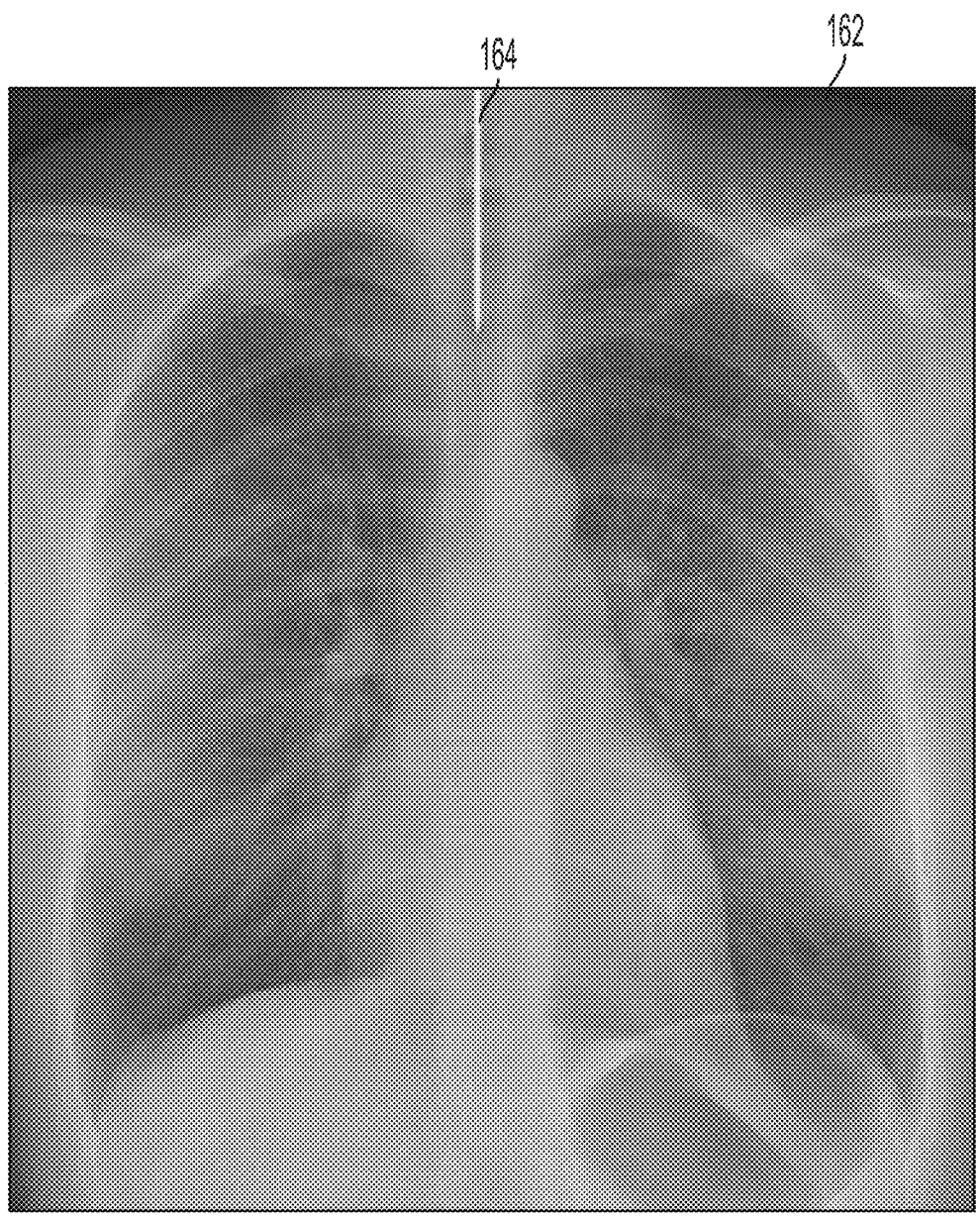
FIG. 7 is an example subsequent x-ray projection generated by the imaging system of FIG. 1.

In step 212, a selected projection angle at which to position the x-ray source 102 and deflector 104 during the procedure is determined as the x-ray imaging device 101 continually or periodically/iteratively captures x-ray images throughout the procedure in order to track the surgical instrument 164 (see FIG. 7). The plurality of annotated initial x-ray projections 160 is reviewed and evaluated to determine which projection angle positions the x-ray source 102 and deflector 104 at a point that maximizes visibility of the planned instrument path in view of the target location as well as obstructing structures, such as bones or organs. In some embodiments, the user selects the selected projection angle for procedure, while in other embodiments, the system 100 automatically identifies the selected projection angle based on factors such as visibility of the target area, visibility of the planned instrument path, positioning of structures, and others.

In embodiments where the annotations 156 includes a plurality of planned instrument paths, the method 200 may include identifying a selected projection angle for each planned instrument path as part of the evaluation of planned instrument paths prior to selection. In other embodiments, the selected planned instrument path may be selected prior to determining the selected projection angle.

In some embodiments, the optimal view of the planned instrument path changes throughout the course of the procedure. A plurality of selected projection angles may be identified, with each selected projection angle being associated with one or more portions of the planned instrument path. The processor 124 may be configured to adjust the location of the x-ray source 102 and deflector 104 during the procedure. For example, the system 100 may track the location of the instrument 164 along the instrument path annotation, which may include location markers for triggering adjustment of the position of the x-ray imaging device 101 from a first selected projection angle to a second selected projection angle.

Referring to step 214, the system 100 captures a plurality of subsequent x-ray projections 162 of the patient at the plurality of projection angles after the x-ray imaging device 101 is positioned in the selected projection angle and the instrument 164 is positioned in the patient's body prior to the start of the procedure. The instrument 164 is generally identifiable in the subsequent x-ray projections 162 as shown in FIG. 7.

Figure 8:
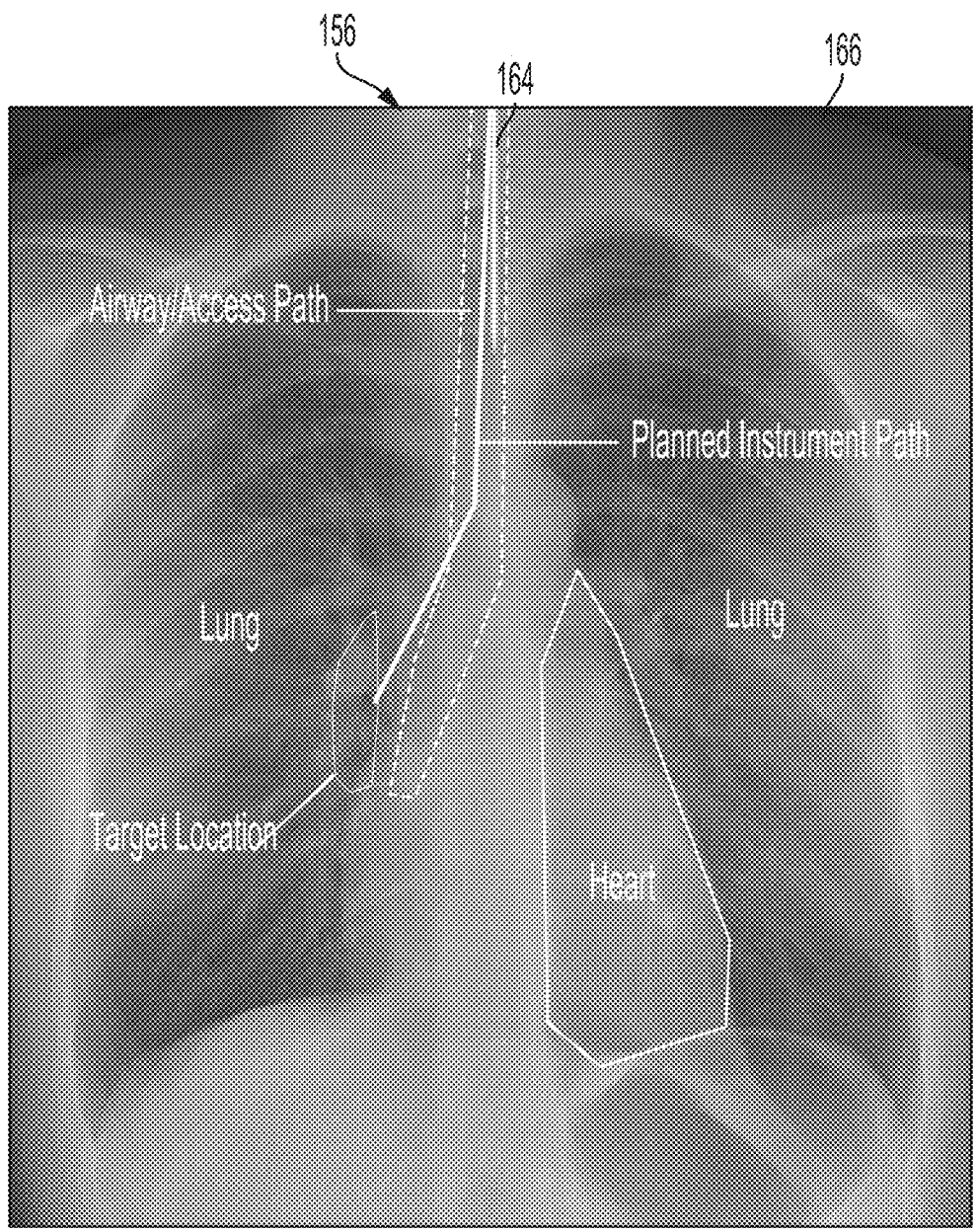
FIG. 8 is an example annotated subsequent x-ray projection generated by the imaging system of FIG. 1.

In step 216, each subsequent x-ray projection 162 is co-registered with a corresponding annotated initial x-ray projection 160 for each projection angle of the plurality of projection angles in order to generate a plurality of annotated subsequent x-ray projections 166. Referring to FIG. 8, the illustrated example annotated subsequent x-ray projections 166 shows the annotations 156 as well as the instrument 164.

Co-registration utilizes structures such as the spine and/or other obvious bone structures appearing in the initial x-ray projection 152 and the subsequent x-ray projection 162 to align images such that the annotations 156 are carried over from the annotated initial x-ray projection 160 to the annotated subsequent x-ray projection 162. The co-registration may be rigid, non-rigid (i.e., allows for deformable or elastic registration in order to match images), or a combination thereof. The images captured by the initial x-ray projection and the subsequent x-ray projection as the same projection angle may be closely aligned but are not absolutely identical due to minor movements of the patient such as respiratory movement. Therefore the x-ray projections 160, 162 are co-registered based on structure appears within each image.

Fluoroscopy x-ray projections are taken periodically throughout the procedure to track the location of the instrument 164, enabling the operating physician to see where the instrument 164 is located within the patient. Steps 214 and 216 are repeated as needed and at additional angles and/or scanner positions in order to ensure that the 3D targeting is on track, providing an increased confidence in the biopsy attack angle. For example, imaging may be repeated at two or more projection angles to confirm targeting from two different angles.

The annotated subsequent x-ray projections 162 are far more useful than the conventional fluoroscopic x-ray projections because the target location and instrument path are identified, enable the physician to move the instrument within the appropriate context illustrated on the imaging.

In the illustrated example as shown in FIG. 1, the axis of rotation X is substantially horizontal. In this example, the patient P is typically lying down on a table XX. Alternatively, the axis of rotation X may be substantially vertical, wherein the patient P is sitting upright.

It should be noted that various changes and modifications to the presently preferred embodiments described herein will be apparent to those skilled in the art. Such changes and modifications may be made without departing from the spirit and scope of the present invention and without diminishing its attendant advantages.

What is claimed is:

1. A system for tracking an instrument during a procedure on a patient, the system comprising:
- a rotatable gantry configured to rotate about an axis of rotation;
- an x-ray imaging device configured to capture x-ray projections, the x-ray imaging device mounted to the rotatable gantry;
- a processor in communication with the x-ray imaging device; and
- a memory coupled to the processor, wherein the memory is configured to store program instructions executable by the controller, and wherein in response to executing the program instructions, the processor is configured to:
  - generate a three dimensional (3D) image of an area including a target location using the x-ray imaging device, wherein the 3D image is based on a plurality of initial x-ray projections taken at a plurality of projection angles;
  - generate an annotated 3D image of the 3D image including annotations of the target location and at least one planned instrument path on the 3D image;
  - generate a plurality of two dimensional (2D) annotations based on the annotated 3D image, each 2D annotation corresponding to a projection angle of the plurality of projection angles;
  - superimpose each 2D annotation onto the initial x-ray projection of the corresponding projection angle to generate a plurality of annotated initial x-ray projections;
  - after positioning the instrument in the patient, obtain a least one subsequent x-ray projection of the patient at a projection angle; and
  - co-register the at least one subsequent x-ray projection with a corresponding annotated initial x-ray projection for the projection angle to generate at least one annotated subsequent x-ray projection.

2. The system of claim 1, wherein the annotations include an access path to the target location and/or a plurality of planned instrument paths.

3. The system of claim 2, wherein the processor is further configured to select a selected planned instrument path from the plurality of planned instrument paths.

4. The system of claim 1, wherein the processor is further configured to identify a selected projection angle for positioning of the x-ray imaging device during the procedure.

5. The system of claim 4, wherein identifying the selected projection angle comprises receiving user input to select the selected projection angle.

6. The system of claim 4, wherein the processor is configured to automatically select the selected projection angle based on one or more factors.

7. The system of claim 1, wherein the plurality of 2D annotations is generated manually, automatically, or a combination thereof.

8. The system of claim 1, wherein the processor is further configured to store the plurality of annotated initial x-ray projections.

9. A method for tracking an instrument during a procedure on a patient, the method comprising:
- generating a three dimensional (3D) image of an area including a target location using the x-ray imaging device, wherein the 3D image is based on a plurality of initial x-ray projections taken at a plurality of projection angles;
- generating an annotated 3D image of the 3D image including annotations of the target location and at least one planned instrument path on the 3D image;
- generating a plurality of two dimensional (2D) annotations based on the annotated 3D image, each 2D annotation corresponding to a projection angle of the plurality of projection angles;
- superimposing each 2D annotation onto the initial x-ray projection of the corresponding projection angle to generate a plurality of annotated initial x-ray projections;
- after positioning the instrument in the patient, obtaining at least one subsequent x-ray projection of the patient at a projection angle; and
- co-registering the at least one subsequent x-ray projection with a corresponding annotated initial x-ray projection for the projection angle to generate at least one annotated subsequent x-ray projection.

10. The method of claim 9, further comprising the step of identifying a selected projection angle for positioning of the x-ray imaging device during the procedure.

* * * * *